United States Patent
Rault et al.

(10) Patent No.: US 6,451,789 B1
(45) Date of Patent: Sep. 17, 2002

(54) 1-AZA-2-ALKY-6-ARYL-CYCLOALKANES

(75) Inventors: Sylvain Rault, Moult; Olivier Renault, Palaiseau; Jean Guillon, Merignac; Patrick Dallemagne, Saint Georges d'Aunay; Pierre Renard, Le Chesnay; Bruno Pfeiffer, Saint Leu la Foret; Pierre Lestage, La Celle Saint Cloud; Marie-Cécile Lebrun, Asnieres, all of (FR)

(73) Assignee: Les Labortoires Servier, Courbevoie (FR)

( * ) Notice: Subject to any disclaimer, the term of this patent is extended or adjusted under 35 U.S.C. 154(b) by 0 days.

(21) Appl. No.: 09/964,085

(22) Filed: Sep. 26, 2001

Related U.S. Application Data

(62) Division of application No. 09/561,646, filed on May 2, 2000, now Pat. No. 6,323,222.

(30) Foreign Application Priority Data

May 3, 1999 (FR) ............................................. 99 05600

(51) Int. Cl.[7] ..................... A61K 31/55; C07D 401/04; C07D 223/02
(52) U.S. Cl. ...................... 514/212; 540/597; 540/604; 540/606; 540/611
(58) Field of Search .......................... 514/212; 540/597, 540/596, 604, 606, 611

(56) References Cited

FOREIGN PATENT DOCUMENTS

| DE | 2013761 | * 10/1971 | ................. 540/596 |
|---|---|---|---|
| EP | 0 159 640 | * 4/1985 | ................. 546/212 |
| EP | 1050530 | * 11/2000 | ................. 514/212 |

* cited by examiner

*Primary Examiner*—Charanjit S. Aulakh
(74) *Attorney, Agent, or Firm*—The Firm of Hueschen and Sage; G. Patrick Sage

(57) ABSTRACT

Compound of formula (I):

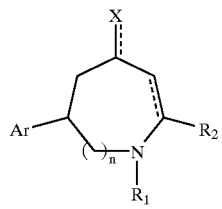

wherein:

n represents 0 or 1, $R_1$ represents hydrogen, arylalkyl, alkyl, acyl, alkoxycarbonyl, arylalkoxycarbonyl or trifluoroacetyl, $R_2$ represents alkyl, X represents oxygen, chlorine, $OR_3$, $SR_4$ or $NOR_5$, $R_3$ represents hydrogen, alkyl, acyl, alkoxycarbonyl or arylalkoxycarbonyl, $R_4$ represents hydrogen, alkyl or aryl, $R_5$ represents hydrogen or optionally substituted alkyl, === represents a single or double bond, Ar represents aryl or heteroaryl, its isomers and addition salts thereof with a pharmaceutically acceptable acid, and medicinal products containing the same which are useful as facilitators of memory and cognition and antalgic agents.

13 Claims, No Drawings

1-AZA-2-ALKY-6-ARYL-CYCLOALKANES

This application is a division of No. 09/561,646 filed May 2, 2000, now U.S. Pat. No. 6,323,222.

BACKGROUND OF THE INVENTION

Ageing of the population due to increased life expectancy has brought with it a major increase in cognitive disorders associated with normal cerebral ageing and with pathological cerebral ageing occurring in the course of neurodegenerative diseases such as, for example, Alzheimer's disease.

The majority of substances used today in treating cognitive disorders associated with ageing act by facilitating the central cholinergic systems—either directly, as in the case of acetylcholinesterase inhibitors (tacrine, donepezil) and cholinergic agonists (nefiracetam), or indirectly, as in the case of nootropic agents (piracetam, pramiracetam) and cerebral vasodilators (vinpocetine).

Besides their cognitive properties, substances acting directly on the central cholinergic systems often have antalgic properties but also have hypothermic properties, which can be undesirable.

It has been therefore been especially valuable to synthesise new compounds that are capable of opposing the cognitive disorders associated with ageing and/or of improving cognitive processes and that can possess antalgic properties without having hypothermic activity.

DESCRIPTION OF THE PRIOR ART

4-Hydroxy- or 4-oxo-substituted 1-aza-2-alkyl-6-aryl-cycloalkanes and 1-aza-2-alkyl-6-aryl-cycloalkenes have already been described in the literature (J. Org. Chem. 1988, 53, 2426; Liebigs Ann. Chem. 1986, 11, 1823; Synlett 1993, 9, 657; Tet. Lett. 1998, 39(3/4), 217), but no pharmacological activity has been described for those compounds.

DETAILED DESCRIPTION OF THE INVENTION

More specifically, the present invention relates to compounds of formula (I):

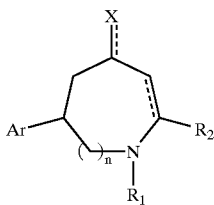

(I)

wherein:

n represents 0 or 1, $R_1$ represents a hydrogen atom or an aryl-$(C_1–C_6)$alkyl group in which the alkyl moiety is linear or branched, a linear or branched $(C_1–C_6)$alkyl group, a linear or branched $(C_1–C_6)$acyl group, a linear or branched $(C_1–C_6)$alkoxycarbonyl group, an aryl-$(C_1–C_6)$-alkoxycarbonyl group in which the alkoxy moiety is linear or branched, or a trifluoro-acetyl group, $R_2$ represents a linear or branched $(C_1–C_6)$alkyl group, X represents an oxygen or chlorine atom or a group $OR_3$, $SR_4$ or $NOR_5$, $R_3$ represents a hydrogen atom or a linear or branched $(C_1–C_6)$alkyl group, a linear or branched $(C_1–C_6)$ acyl group, a linear or branched $(C_1–C_6)$ alkoxycarbonyl group or an aryl-$(C_1–C_6)$ alkoxycarbonyl group in which the alkoxy moiety is linear or branched, $R_4$ represents a hydrogen atom or a linear or branched $(C_1–C_6)$alkyl group or an aryl group, $R_5$ represents a hydrogen atom or a linear or branched $(C_1–C_6)$alkyl group optionally substituted by one or more identical or different groups selected from hydroxy, amino (optionally substituted by one or two linear or branched $(C_1–C_6)$alkyl groups) and linear or branched $(C_1–C_6)$alkoxy, === represents a single or double bond, it being understood that the valency of the atoms is respected, Ar represents an aryl group or a heteroaryl group, their isomers and addition salts thereof with a pharmaceutically acceptable acid, with the proviso that the compounds of formula (I) are other than:

6-methyl-2-phenyl-2,3-dihydro-4-pyridinone, 2-methyl-6-phenyl-4-piperidinone,

N-benzyl-2-(R'$_2$)-6-phenyl-4-piperidinones wherein R'$_2$ represents a methyl, ethyl, propyl or isopropyl group, and 2-(R"$_2$)-6-phenyl-4-piperidinols wherein R"$_2$ represents an isopropyl or butyl group.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid etc.

An aryl group is understood to be phenyl, biphenylyl, naphthyl or tetrahydronaphthyl, each of those groups being optionally substituted by one or more identical or different groups selected from halogen, linear or branched $(C_1–C_6)$ alkyl, hydroxy, linear or branched $(C_1–C_6)$alkoxy, trihalomethyl and amino (optionally substituted by one or more linear or branched $(C_1–C_6)$alkyl groups).

A heteroaryl group is understood to be an aromatic, mono- or bi-cyclic, 5- to 12-membered group containing one, two or three hetero atoms selected from oxygen, nitrogen and sulphur, it being understood that the heteroaryl group may be optionally substituted by one or more identical or different groups selected from halogen, linear or branched $(C_1–C_6)$ alkyl, hydroxy, linear or branched $(C_1–C_6)$alkoxy, trihalomethyl and amino (optionally substituted by one or more linear or branched $(C_1–C_6)$alkyl groups). Among the heteroaryl groups there may be mentioned, without implying any limitation, thienyl, pyridyl, furyl, pyrrolyl, imidazolyl, oxazolyl, isoxazolyl, thiazolyl and isothiazolyl groups.

Preferred compounds of formula (I) are those wherein n represents 0.

The group X as defined for formula (I) is preferably an oxygen atom or a group $OR_3$ wherein $R_3$ represents a hydrogen atom.

The group $R_1$ as defined for formula (I) is preferably a hydrogen atom.

The term "aryl" used in respect of the group Ar as defined for formula (I) is preferably an optionally substituted phenyl group.

The term "heteroaryl" used in respect of the group Ar as defined for formula (I) is preferably an optionally substituted thienyl group or an optionally substituted pyridyl group.

The invention relates also to a process for the preparation of compounds of formula (I), which process is characterised in that a compound of formula (II):

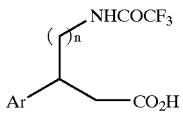
(II)

wherein Ar and n are as defined for formula (I), is reacted with thionyl chloride to yield the corresponding acid chloride, which is reacted with a compound of formula (III):

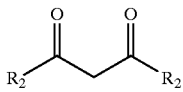
(III)

wherein $R_2$ is as defined for formula (I), in the presence of samarium triiodide, to yield, after deprotection by an acid HA, the compound of formula (IV):

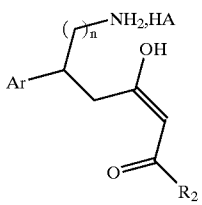
(IV)

wherein Ar, n and $R_2$ are as defined hereinbefore and HA represents a proton donor acid, which compound of formula (IV) is then reacted in a basic medium to yield the compound of formula (Ia), a particular case of the compounds of formula (I):

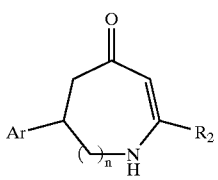
(Ia)

wherein Ar, n and $R_2$ are as defined hereinbefore, which compound of formula (Ia) is condensed, if desired, with a compound of formula $R'_1$—Y, wherein $R'_1$, represents an aryl-($C_1$–$C_6$)alkyl group in which the alkyl moiety is linear or branched, a linear or branched ($C_1$–$C_6$)alkyl group, a linear or branched ($C_1$–$C_6$)acyl group, a linear or branched ($C_1$–$C_6$)alkoxycarbonyl group, an aryl-($C_1$–$C_6$)alkoxycarbonyl group in which the alkoxy moiety is linear or branched, or a trifluoroacetyl group and Y represents a leaving group, to yield the compound of formula (Ib), a particular case of the compounds of formula (I):

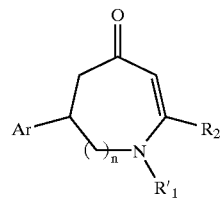
(Ib)

wherein Ar, n, $R'_1$ and $R_2$ are as defined hereinbefore, which compound of formula (Ia) or (Ib) is converted, if desired, either by partial reduction with the aid of an appropriate reducing agent, followed, if desired, by alkylation, acylation or esterification of the hydroxy function to yield the compound of formula (Ic), a particular case of the compounds of formula (I):

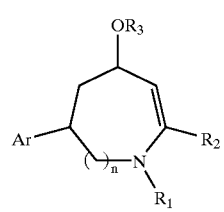
(Ic)

wherein Ar, n and $R_2$ are as defined hereinbefore and $R_1$ and $R_3$ are as defined for formula (I), or by complete reduction with the aid of an appropriate reducing agent to yield the compound of formula (Id), a particular case of the compounds of formula (I):

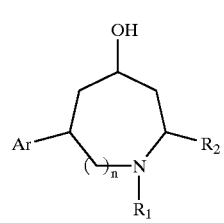
(Id)

wherein Ar, n, $R_1$ and $R_2$ are as defined hereinbefore, which compound of formula (Id) is reacted, if desired, either with a compound of formula $R'_3$—Y, wherein $R'_3$ represents a linear or branched ($C_1$–$C_6$)alkyl group, a linear or branched ($C_1$–$C_6$)acyl group, a linear or branched ($C_1$–$C_6$)alkoxycarbonyl group or an aryl-($C_1$–$C_6$)alkoxycarbonyl group in which the alkoxy moiety is linear or branched and Y represents a leaving group, to yield the compound of formula (Ie), a particular case of the compounds of formula (I):

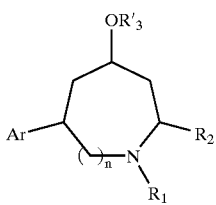

(Ie)

wherein Ar, n, $R_1$, $R_2$ and $R'_3$ are as defined hereinbefore, or in an oxidation reaction using an appropriate oxidising agent, to form an oxo group, yielding the compound of formula (If), a particular case of the compounds of formula (I):

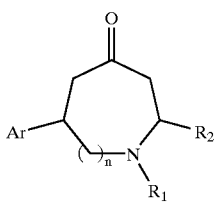

(If)

wherein Ar, n, $R_1$ and $R_2$ are as defined hereinbefore, which compounds of formula (Ia), (Ib) or (If) are reacted, if desired, either with a chlorinating agent such as, for example, thionyl chloride to yield the compound of formula (Ig), a particular case of the compounds of formula (I):

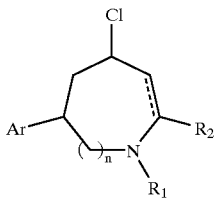

(Ig)

wherein Ar, n, $R_1$ and $R_2$ are as defined hereinbefore and === is as defined for formula (I), which is reacted, if desired, with a compound of formula $HSR_4$, wherein $R_4$ is as defined for formula (I), to yield the compound of formula (Ih), a particular case of the compounds of formula (I):

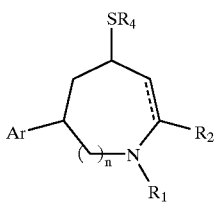

(Ih)

wherein Ar, n, $R_1$, $R_2$, $R_4$ and === are as defined for formula (I), or with a compound of formula $H_2N\text{-}OR_5$, wherein $R_5$ is as defined for formula (I), to yield the compound of formula (Ii), a particular case of the compounds of formula (I):

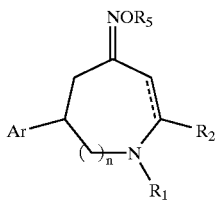

(Ii)

wherein Ar, n, $R_1$, $R_2$, $R_5$ and === are as defined hereinbefore, the compounds of formulae (I/a), (Ib), (Ic), (Id), (Ie), (If), (Ig), (Ih) and (Ii) constituting the totality of the compounds of formula (I), which are purified, if necessary, according to a conventional purification technique, are separated, if desired, into their isomers according to a conventional separation technique and are converted, if desired, into their addition salts with a pharmaceutically acceptable acid.

The compound of formula (II) is obtained by starting from the compound of formula (VI):

Ar—CHO  (VI)

wherein Ar is as defined hereinbefore, which is converted into a compound of formula (VII):

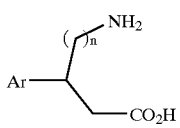

(VII)

wherein Ar and n are as defined hereinbefore,
when n is 0, according to the procedure described by W. M. Rodionow and E. Th. Malewinskaya in Ber. 1926, 59, 2952 and T. B. Johnson, J. E. Livak in J. Am. Chem. Soc. 1936, 58, 299
when n is 1, according to the procedure described by Keberle in Patent Specification CH 449046,
which compound of formula (VII) is optionally resolved (when it is desired to obtain the compound of formula (I) in its enantiomerically pure form) according to a conventional resolution technique before being converted into a compound of formula (II) by reaction with trifluoroacetic anhydride.

In addition to the fact that the compounds of the present invention are new, they exhibit properties facilitating cognitive processes and antalgic properties, rendering them of use in the treatment of cognitive deficiencies associated with cerebral ageing and with neurodegenerative pathologies, such as Alzheimer's disease, Parkinson's disease, Pick's disease, Korsakoffs disease and frontal lobe and subcortical dementias and in the treatment of pain.

The invention relates also to pharmaceutical compositions comprising as active ingredient a compound of formula (I) together with one or more appropriate, inert, non-toxic excipients. Among the pharmaceutical compositions according to the invention there may be mentioned more especially those that are suitable for oral, parenteral (intravenous or subcutaneous) and nasal administration, tablets or dragees, sublingual tablets, gelatin capsules, lozenges, suppositories, creams, ointments, dermal gels, injectable preparations, drinkable suspensions etc.

The dosage used can be adapted to the nature and the severity of the disorder, the administration route and the age and weight of the patient. The dosage varies from 1 to 500 mg per day in one or more administrations.

The following Examples illustrate the invention without limiting it in any way. DMSO is to be understood as meaning dimethylsulfoxide.

A compound having the relative configuration (2R*, 4S*, 6R*) is understood to be a racemic mixture of the compounds having the absolute configurations (2R, 4S, 6R) and (2S, 4R, 6S).

The starting materials used are products that are known or prepared according to known procedures.

The structures of the compounds described in the Examples were determined according to customary spectrophotometric techniques (infrared, NMR, mass spectrometry).

EXAMPLE 1

(±)-2-(3-Chlorophenyl)-6-methyl-2,3-dihydro-4(1H)-pyridinone

Step A: (±)-3-(3-Chlorophenyl)-β-alanine

The expected product is obtained according to the procedure described in Ber. 1926, 59, 2952 and JACS 1936, 58, 299, starting from 3-chlorobenzaldehyde.

Step B: (±)-3-(3-Chlorophenyl)-N-trifluoroacetyl-β-alanine

Trifluoroacetic anhydride (11 mmol) is added to 10 mmol of the compound obtained in the preceding Step. After stirring for 30 minutes, the solvent and the excess reagent are evaporated off under reduced pressure to yield the expected product.

Step C: (±)-3-(3-Chlorophenyl)-3-trifluoroacetylaminopropionic acid chloride 20 ml of thionyl chloride are added to 10 mmol of the compound described in the preceding Step and the mixture is then heated to reflux. After 80 minutes, the thionyl chloride is evaporated off and the residue is then taken up in 50 ml of petroleum ether. The precipitate obtained is filtered off and washed with petroleum ether.

Step D: (±)-1-(3-Chlorophenyl)-3-hydroxy-5-oxo-3-hexenylammonium chloride 11 mmol of samarium and 16.5 mmol of iodine are reacted in dry acetonitrile. After stirring for 12 hours at ambient temperature, the solution is cooled to 0° C., and then the acid chloride obtained in the preceding Step (10 mmol) and 11 mmol of pentane-2,4-dione are added. The reaction mixture is stirred for 6 hours at 0° C. 50 ml of hydrochloric acid solution (6N) are added, the acetonitrile is evaporated off and then 50 ml of hydrochloric acid (6N) are added. The aqueous phase is extracted with ether. The combined organic phases are washed with saturated sodium bicarbonate solution and then with saturated sodium thiosulphate solution and they are then dried and evaporated. The solid residue is taken up in a 50/50 mixture of hydrochloric acid and ethanol; the suspension is heated at reflux for 12 hours and then evaporated to yield the expected product in the form of yellow crystals.

Melting point: 97° C.

IR (KBr):

OH band at 3415 cm$^{-1}$ $NH_3^+$ band between 3255 and 2500 cm$^{-1}$

CO band at 1725 cm$^{-1}$

Step E: (±)-2-(3-Chlorophenyl)-6-methyl-2,3-dihydro-4(1H)-pyridinone

Concentrated ammonium hydroxide solution is added dropwise to 10 mmol of the compound obtained in the preceding Step dissolved in dichloromethane, until the pH of the mixture is ≧10.

The aqueous phase is extracted with dichloromethane; the combined organic phases are then dried and evaporated. The oily residue is taken up in 50 ml of ether. By filtering off the precipitate obtained, the expected product is obtained in the form of beige-coloured crystals.

Melting point: 163° C.

Elementary microanalysis:

|  | % C | % H | % N |
| --- | --- | --- | --- |
| calculated | 65.02 | 5.91 | 6.32 |
| found | 64.89 | 6.02 | 6.25 |

EXAMPLE 2

(±)-N-Methyl-2-(3-chlorophenyl)-6-methyl-2,3-dihydro-4-(1H)-pyridinone

A 1.6M solution of n-butyllithium in hexane (11 mmol) is added dropwise, at −78° C., to 10 mmol of the compound described in Example 1 dissolved in tetrahydrofuran. After stirring for half an hour at −78° C., 11 mmol of iodomethane are added. Stirring is continued at −78° C. for a further 30 minutes and then at ambient temperature for 1 hour. After hydrolysing by adding saturated sodium hydrogen carbonate solution, the aqueous phase is extracted with dichloromethane. The combined organic phases are washed, dried and evaporated to yield the expected product in the form of orange crystals.

Melting point: 82° C.

Elementary microanalysis:

|  | % C | % H | % N |
| --- | --- | --- | --- |
| calculated | 57.39 | 6.23 | 3.94 |
| found | 57.82 | 6.21 | 3.78 |

EXAMPLE 3

(2R*,4S*,6R*)-N-Methyl-2-(3-chlorophenyl)-6-methyl-4-piperidinol fumarate

Step A: (2R*, 4S*, 6R*)-N-Methyl-2-(3-chlorophenyl)-6-methyl-4-piperidinol 80 mmol of sodium borohydride are added to a solution, at 0° C., in ethanol, of 10 mmol of the compound described in Example 2. After stirring for 12 hours at ambient temperature, the ethanol is evaporated off and the white residue is taken up in dichloromethane. The organic phase is washed with 2N hydrochloric acid solution; the combined aqueous phases are then saturated with sodium chloride, rendered alkaline with concentrated ammonium hydroxide solution and then extracted with dichloromethane. The combined organic phases are dried and then evaporated to yield the expected product in the form of a colourless oil.

Step B: (2R*, 4S*, 6R*)-N-Methyl-2-(3-chlorophenyl)-6-methyl-4-piperidinol fumarate 11 mmol of fumaric acid are added to a solution, in isopropanol, of 10 mmol of the compound obtained in the preceding Step. After stirring for 1 hour at ambient temperature, the solvents are evaporated off to yield the expected product in the form of white crystals.

Melting point: 182° C.

EXAMPLE 4

(2R*,4S*,6R*)-N-Methyl-2-(3-chlorophenyl)-4-methoxy-6-methyl-piperidine 10 mmol of the compound described in Example 3 are added, at 0° C., to 11 mmol of sodium hydride suspended in tetrahydrofuran. After stirring for half an hour at 0° C., 100 mmol of iodomethane are added. Stirring is then continued at ambient temperature for 2 days; the solution is then hydrolysed by adding 1N hydrochloric acid solution. The aqueous phase is extracted with dichloromethane; the combined organic phases are then washed, dried and evaporated to yield the expected product in the form of a pale yellow oil.

EXAMPLE 5

(2R*,4S*)-N-Methyl-2-(3-chlorophenyl)-6-methyl-1,2,3,4-tetrahydro-4-pyridinol

To a solution, in ethanol, of 10 mmol of the compound described in Example 2 there are added 10 mMol of $CeCl_3$ heptahydrate and then, at 0° C. and in portions, 10 mmol of sodium borohydride. After stirring for half an hour at 0° C. and then for 1 hour at ambient temperature, the ethanol is evaporated off and the white residue is taken up in dichloromethane. The organic phase is washed with 2N hydrochloric acid solution; the combined aqueous phases are then saturated with sodium chloride, rendered basic with concentrated ammonium hydroxide solution and then extracted with dichloromethane. The combined organic phases are dried and then evaporated to yield the expected product.

EXAMPLE 6

(2R*,4S*,6R*)-2-(3-Chlorophenyl)-6-methyl-4-piperidinol hydrochloride

Step A (2R*,4S*,6R*)-2-(3-Chlorophenyl)-6-methyl-4-piperidinol

The expected product is obtained according to the procedure described in Step A of Example 3, starting from the compound described in Example 1.

Step B: (2R*, 4S*, 6R*)-2-(3-Chlorophenyl)-6-methyl-4-piperidinol hydrochloride 11 ml of a 1M solution of ethereal HCl are added to a solution, in isopropanol, of 10 mmol of the compound obtained in the preceding Step. After stirring for 1 hour at ambient temperature, the solvents are evaporated off to yield the expected product in the form of beige-coloured crystals.

Melting point: 248° C.
Elementary microanalysis:

|            | % C   | % H  | % N  |
|------------|-------|------|------|
| calculated | 45.82 | 6.53 | 5.34 |
| found      | 45.54 | 6.62 | 5.41 |

EXAMPLE 7

(2R*,4S*,6R*)-2-(3-Chlorophenyl)-6-methyl-4-piperidinol oxalate 11 mmol of oxalic acid are added to a solution, in isopropanol, of 10 mmol of the compound obtained in Step A of Example 6. After stirring for 1 hour at ambient temperature, the solvents are evaporated off to yield the expected product in the form of crystals.

Melting point: 224° C.

EXAMPLE 8

(2R*,4S*,6R*)-N-Trifluoroacetyl-2-(3-chlorophenyl)-6-methyl-4-piperidinol hydrochloride Step A: (±)-N-Trifluoroacetyl-2-(3-chlorophenyl)-6-methyl-2,3-dihydro-4(1H)-pyridinone The expected product is obtained according to the procedure described in Example 2, starting from the compound described in Example 1 and replacing the iodomethane by trifluoroacetyl chloride.

Step B: (2R*, 4S*, 6R*)-N-Trifluoroacetyl-2-(3-chlorophenyl)-6-methyl-4-piperidinol hydrochloride Starting from the compound obtained in the preceding Step, the expected product is obtained according to the procedure described in Example 6.

EXAMPLE 9

(2R*,4S*)-2-(3-Chlorophenyl)-6-methyl-1,2,3,4-tetrahydro-4-pyridinol

The expected product is obtained according to the procedure described in Example 5, starting from the compound described in Example 1.

EXAMPLE 10

Benzyl (2R*,4S*,6R*)-2-(3-chlorophenyl)-6-methyl-4-oxo-3,4-dihydro-1(2H)-pyridinecarboxylate The expected product is obtained according to the procedure described in Example 2, starting from the compound described in Example 1 and replacing the iodomethane by benzyl chloroformate.

EXAMPLE 11

Benzyl (2R*,4S*)-2-(3-chlorophenyl)-4-hydroxy-6-methyl-3,4-dihydro-1(2H)-pyridinecarboxylate The expected product is obtained according to the procedure described in Example 5, starting from the compound described in Example 10.

EXAMPLE 12

(2R*,6R*)-2-(3-Chlorophenyl)-6-methyl-4-piperidinone oxalate

Step A: (2R*, 6R*)-2-(3-Chlorophenyl)-6-methyl-4-piperidinone 20 mmol of orthophosphoric acid and then 20 mmol of chromic anhydride are added dropwise to a solution, in acetone, at 0° C., of 10 mmol of the compound described in Step A of Example 6.

After stirring for 1 hour at 0° C. and then for 12 hours at ambient temperature, the acetone is evaporated off; the residue is taken up in 20 ml of ice and then rendered alkaline (pH>10) using 28% ammonium hydroxide solution. The solution is then extracted with dichloro-methane. The combined organic phases are dried and then evaporated to yield the expected product.

Step B: (2R*,6R*)-2-(3-Chlorophenyl)-6-methyl-4-piperidinone oxalate

The expected product is obtained according to the procedure described in Example 7, starting from the compound obtained in the preceding Step.

Melting point: 183° C.

EXAMPLE 13

(2R*,4R*,6R*)-4-Chloro-2-(3-chlorophenyl)-6-methyl-piperidine fumarate

Step A: (2R*,4R*,6R*)-4-Chloro-2-(3-chlorophenyl)-6-methyl-piperidine

To a solution, in chloroform, of 10 mmol of the compound described in Step A of Example 12 there are added 20 mmol of triethylamine followed by 20 mmol of thionyl chloride. The reaction mixture is heated at reflux for 2 hours. After returning to ambient temperature, the organic phase is washed; the combined aqueous phases are rendered alkaline by the addition of ammonium hydroxide solution and then extracted with dichloromethane, and the combined organic phases are washed, dried and evaporated to yield the expected product.

Step B: (2R*,4R*,6R*)-4-Chloro-2-(3-chlorophenyl)-6-methyl-piperidine fumarate

The expected product is obtained according to the procedure described in Step B of Example 3, starting from the compound obtained in the preceding Step.

Melting point: 203° C.

EXAMPLE 14

(2R*,4S*,6R*)-2-(3-Chlorophenyl)-6-methyl-4-phenylthio-piperidine fumarate

Step A: (2R*,4S*,6R*)-2-(3-Chlorophenyl)-6-methyl-4-phenylthio-piperidine

To 30 mmol of sodium hydride suspended in dimethylformamide there are added, at 0° C., 13 mmol of thiophenol and then, after stirring for 30 minutes, 10 mmol of the compound described in Step A of Example 13. The reaction mixture is then heated at reflux for 2 hours and the solution is subsequently hydrolysed by adding 1N hydrochloric acid solution. The aqueous phase is washed with ether and is then rendered alkaline by the addition of ammonium hydroxide solution and extracted with ether. The combined organic phases are washed with water, dried and then evaporated to yield the expected product.

Step B: (2R*,4S*, 6R*)-2-(3-Chlorophenyl)-6-methyl-4-phenylthio-piperidine fumarate The expected product is obtained according to the procedure described in Step B of Example 3, starting from the compound obtained in the preceding Step.

Melting point: 181 ° C.

EXAMPLE 15

(±)-2-(3-Chlorophenyl)-6-methyl-2,3-dihydro-4 (1H)-pyridinone oxime 40 mmol of hydroxylamine hydrochloride and 40 mmol of sodium acetate are added to a solution, in ethanol, of 10 mmol of the compound described in Example 1, and the reaction mixture is then heated at reflux for 2 hours. After hydrolysis, the aqueous phase is extracted with dichloromethane; the combined organic phases are then washed, dried and evaporated to yield the expected product in the form of orange crystals.

Melting point: 88° C. (Z/E mixture 20/80)

Elementary microanalysis:

|  | % C | % H | % N |
| --- | --- | --- | --- |
| calculated | 60.89 | 5.54 | 11.83 |
| found | 60.95 | 5.62 | 11.15 |

EXAMPLE 16

(2R)-2-(3-Chlorophenyl)-6-methyl-2,3-dihydro-4-(1H)-pyridinone

Step A: (±)-N-Phenylacetyl-3-(3-chlorophenyl)-β-alanine

To a solution, in a 3/1 mixture of water/acetone, of 10 mmol of (±)-3-(3-chlorophenyl)-β-alanine described in Step A of Example 1 there are added 24 mmol of triethylamine and then, at −5° C., 13 mmol of phenylacetyl chloride. After stirring for 2 hours at −5° C. and then for 3 hours at ambient temperature, the solution is filtered; the acetone is evaporated off, the aqueous phase is washed with ether and is then acidified to pH=1 and extracted with ethyl acetate. The combined organic phases are dried and then evaporated. The residue obtained is washed with hexane, precipitated in a minimum of ether and then filtered to yield the expected product.

Step B: (3R)-3-(3-Chlorophenyl)-β-alanine hydrochloride

Penicillin amidase (20 mg) is introduced into 10 mmol of the compound described in the preceding Step in saturated sodium bicarbonate solution at 37° C. after adjustment of the pH to from 7.4 to 7.6 using concentrated hydrochloric acid. After stirring for 24 hours at a pH of from 7.5 to 8, the mixture is brought to pH=1 with hydrochloric acid. The aqueous phase is washed with ether and then evaporated. The white solid obtained is taken up in ethanol and then filtered. The filtrate is then evaporated to yield the expected product.

Step C: (2R)-2-(3-Chlorophenyl)-6-methyl-2,3-dihydro-4-(1H)-pyridinone

The expected product is obtained according to the procedure described in Steps B to E of Example 1, starting from the compound described in the preceding Step.

Rotatory power: $[\alpha]^{20}_D = -176.92$ (c=0.0039; $CH_3OH$)

EXAMPLE 17

(2R,4S,6R)-2-(3-Chlorophenyl)-6-methyl-4-piperidinol oxalate

Step A: (2R,4S,6R)-2-(3-Chlorophenyl)-6-methyl-4-piperidinol

The expected product is obtained according to the procedure described in Step A of Example 3, starting from the compound described in Example 16.

Step B: (2R, 4S, 6R)-2-(3-Chlorophenyl)-6-methyl-4-piperidinol oxalate

The expected product is obtained according to the procedure described in Example 7, starting from the compound obtained in the preceding Step.

Rotatory power: $[\alpha]^{20}_D = -9.58$ (c=0.0024; $H_2O$)

EXAMPLE 18

(2S)-2-(3-Chlorophenyl)-6-methyl-2,3-dihydro-4-(1H)-pyridinone

Step A: (3S)-3-(3-Chlorophenyl)-β-alanine hydrochloride

Penicillin amidase (20 mg) is introduced into 10 mmol of the compound described in Step A of Example 16 in saturated sodium bicarbonate solution at 37° C. after adjustment of the pH to from 7.4 to 7.6 using concentrated hydrochloric acid. After stirring for 24 hours at a pH of from 7.5 to 8, the mixture is brought to pH=1 with hydrochloric acid. The aqueous phase is extracted with ether and then the organic phases obtained are combined, dried and evaporated. The residue is taken up in hexane and precipitated using a minimum of ether. After filtration, the solid obtained is heated at 50° C. for 24 hours in 2N hydrochloric acid to yield the expected product.

Step B: (2S)-2-(3-Chlorophenyl)-6-methyl-2,3-dihydro-4-(1H)-pyridinone

The expected product is obtained according to the procedure described in Steps B to E of Example 1, starting from the compound described in the preceding Step.

Rotatory power: $[\beta]^{20}_D = +179.7$ (c=0.080; $CH_3OH$)

EXAMPLE 19

(2S,4R,6S)-2-(3-Chlorophenyl)-6-methyl-4-piperidinol fumarate

Step A: (2S,4R,6S)-2-(3-Chlorophenyl)-6-methyl-4-piperidinol

The expected product is obtained according to the procedure described in Step A of Example 3, starting from the compound described in Example 18.

Step B: (2S,4R,6S)-2-(3-Chlorophenyl)-6-methyl-4-piperidinol fumarate

The expected product is obtained according to the procedure described in Step B of Example 3, starting from the compound obtained in the preceding Step.

Rotatory power: $[\alpha]^{20}_D$=+9.8 (c=0.067; DMSO)

EXAMPLE 20

(2S,6S)-2-(3-Chlorophenyl)-6-methyl-4-piperidinone oxalate

The expected product is obtained according to the procedure described in Example 12, starting from the compound described in Step A of Example 19.

Melting point: 184° C.
Rotatory power: $[\alpha]^{20}_D$=−24.2 (c=0.065; DMSO)

EXAMPLE 21

(2R*,4S*,6R*)-2-Phenyl-6-methyl-4-piperidinol hydrochloride

Step A: (±)-2-Phenyl-6-methyl-2,3-dihydro-1H-4-pyridinone

The expected product is obtained according to the procedure described in Example 1, starting from benzaldehyde. Yellow crystals.

Melting point: 156° C.
Elementary microanalysis:

|  | % C | % H | % N |
| --- | --- | --- | --- |
| calculated | 76.97 | 7.00 | 7.18 |
| found | 76.69 | 7.11 | 7.39 |

Step B: (2R*,4S*,6R*)-2-Phenyl-6-methyl-4-piperidinol

The expected product is obtained according to the procedure described in Step A of Example 3, starting from the compound obtained in the preceding Step.

Step C: (2R*,4S*,6R*)-2-Phenyl-6-methyl-4-piperidinol hydrochloride

The expected product is obtained according to the procedure described in Step B of Example 6, starting from the compound obtained in the preceding Step. Beige crystals.

Melting point: 236° C.
Elementary microanalysis:

|  | % C | % H | % N |
| --- | --- | --- | --- |
| calculated | 63.29 | 7.97 | 6.15 |
| found | 62.95 | 8.09 | 5.99 |

EXAMPLE 22

(2R*,4S*,6R*)-2-Phenyl-6-methyl-4-piperidinol oxalate

The expected product is obtained according to the procedure described in Example 7, starting from the compound described in Step B of Example 21.

EXAMPLE 23

(±)-2-(2-Chlorophenyl)-6-methyl-2,3-dihydro-4(1H)-pyridinone

The expected product is obtained according to the procedure described in Example 1, starting from 2-chlorobenzaldehyde. Beige crystals.

Melting point: 98° C.

Elementary microanalysis:

|  | % C | % H | % N |
| --- | --- | --- | --- |
| calculated | 65.02 | 5.91 | 6.32 |
| found | 65.20 | 5.93 | 6.32 |

EXAMPLE 24

(±)-2-(4-Chlorophenyl)-6-methyl-2,3-dihydro-4(1H)-pyridinone

The expected product is obtained according to the procedure described in Example 1, starting from 4-chlorobenzaldehyde. Beige crystals.

Melting point: 104° C.
Elementary microanalysis:

|  | % C | % H | % N |
| --- | --- | --- | --- |
| calculated | 65.02 | 5.91 | 6.32 |
| found | 64.90 | 5.92 | 6.31 |

EXAMPLE 25

(±)-6-(4-Chlorophenyl)-2-methyl-1,5,6,7-tetrahydro-4H-azepin-4-one

4-Amino-3-(4-chlorophenyl)butyric acid (baclofen) is subjected to the operations described in Steps B to E of Example 1, to yield the expected product in the form of cream crystals.

Melting point: 118° C.
Elementary microanalysis:

|  | % C | % H | % N |
| --- | --- | --- | --- |
| calculated | 66.24 | 5.99 | 5.84 |
| found | 66.25 | 5.84 | 6.17 |

EXAMPLE 26

(±)-2-(3,4-Dichlorophenyl)-6-methyl-2,3-dihydro-4(1H)-pyridinone

The expected product is obtained according to the procedure described in Example 1, starting from 3,4-dichlorobenzaldehyde. Beige crystals.

Melting point: 163° C.
Elementary microanalysis:

|  | % C | % H | % N |
| --- | --- | --- | --- |
| calculated | 56.27 | 4.33 | 5.47 |
| found | 56.27 | 4.33 | 5.45 |

EXAMPLE 27

(±)-2-(3-Methoxyphenyl)-6-methyl-2,3-dihydro-4(1H)-pyridinone

The expected product is obtained according to the procedure described in Example 1, starting from 3-methoxybenzaldehyde. Beige crystals.

Melting point: 98° C.

EXAMPLE 28

(±)-6-Methyl-2-(2-thienyl)-2,3-dihydro-4(1H)-pyridinone

The expected product is obtained according to the procedure described in Example 1, starting from thiophene-2-carboxaldehyde. Beige crystals.

Melting point: 114° C.

Elementary microanalysis:

|  | % C | % H | % N |
|---|---|---|---|
| calculated | 62.15 | 5.74 | 7.25 |
| found | 62.30 | 5.81 | 7.08 |

EXAMPLE 29

(2R*,4S*,6R*)-6-Methyl-2-(2-thienyl)-4-piperidinol hydrochloride

The expected product is obtained according to the procedure described in Example 6, starting from the compound described in Example 28. Beige crystals.

Melting point: 248° C.

Elementary microanalysis:

|  | % C | % H | % N |
|---|---|---|---|
| calculated | 51.38 | 6.90 | 5.99 |
| found | 51.16 | 7.01 | 5.79 |

EXAMPLE 30

(±)-6-Methyl-2-(3-thienyl)-2,3-dihydro-4(1H)-pyridinone

The expected product is obtained according to the procedure described in Example 1, starting from thiophene-3-carboxaldehyde. Brown crystals.

Melting point: 103° C.

Elementary microanalysis:

|  | % C | % H | % N |
|---|---|---|---|
| calculated | 62.15 | 5.74 | 7.25 |
| found | 62.27 | 5.82 | 7.20 |

EXAMPLE 31

(2R*,4S*,6R*)-6-Methyl-2-(3-thienyl)4-piperidinol hydrochloride

Step A: (2R*,4S*,6R*)-6-Methyl-2-(3-thienyl)-4-piperidinol

The expected product is obtained according to the procedure described in Step A of Example 3, starting from the compound described in Example 30.

Step B: (2R*,4S*,6R*)-6-Methyl-2-(3-thienyl)-4-piperidinol hydrochloride

The expected product is obtained according to the procedure described in Step B of Example 6, starting from the compound described in the preceding Step. Beige crystals.

Melting point: 241° C.

Elementary microanalysis:

|  | % C | % H | % N |
|---|---|---|---|
| calculated | 51.38 | 6.90 | 5.99 |
| found | 51.26 | 6.81 | 5.81 |

EXAMPLE 32

(2R*,4S*,6R*)-6-Methyl-2-(3-thienyl)-4-piperidinol oxalate

The expected product is obtained according to the procedure described in Example 7, starting from the compound described in Step A of Example 31.

Melting point: 246° C.

EXAMPLE 33

(2R*,6R*)-6-Methyl-2-(3-thienyl)-4-piperidinone oxalate

The expected product is obtained according to the procedure described in Example 12, starting from the compound described in Step A of Example 31.

Melting point: 184° C.

EXAMPLE 34

(±)-2-(4-Bromo-2-thienyl)-6-methyl-2,3-dihydro-4(1H)-pyridinone

The expected product is obtained according to the procedure described in Example 1, starting from 4-bromo-thiophene-2-carboxaldehyde. Beige crystals.

Melting point: 170° C.

Elementary microanalysis:

|  | % C | % H | % N |
|---|---|---|---|
| calculated | 44.13 | 3.70 | 5.15 |
| found | 44.01 | 3.78 | 5.06 |

EXAMPLE 35

(±)-2-(4-Chloro-2-thienyl)-6-methyl-2,3-dihydro-4(1H)-pyridinone

The expected product is obtained according to the procedure described in Example 1, starting from 4-chloro-thiophene-2-carboxaldehyde. Beige crystals.

Melting point: 141° C.

Elementary microanalysis:

|  | % C | % H | % N |
|---|---|---|---|
| calculated | 52.75 | 4.43 | 6.15 |
| found | 52.52 | 4.49 | 6.01 |

EXAMPLE 36

(±)-6-Methyl-2-(3-pyridyl)-2,3-dihydro-4(1H)-pyridinone

The expected product is obtained according to the procedure described in Example 1, starting from nicotinaldehyde. Yellow crystals.

Melting point: 141° C.
Elementary microanalysis:

|  | % C | % H | % N |
|---|---|---|---|
| calculated | 52.75 | 4.43 | 6.15 |
| found | 52.52 | 4.49 | 6.01 |

EXAMPLE 37

(2R*,4S*,6R*)-6-Methyl-2-(3-pyridyl)-4-piperidinol dioxalate

Step A: (2R*,4S*,6R*)-6-Methyl-2-(3-pyridyl)-4-piperidinol

The expected product is obtained according to the procedure described in Step A of Example 3, starting from the compound described in Example 36.

Step B: (2R*,4S*,6R*)-6-Methyl-2-(3-pyridyl)-4-piperidinol dioxalate 22 mmol of oxalic acid are added to a solution, in isopropanol, of 10 mmol of the compound obtained in the preceding Step. After stirring for 1 hour at ambient temperature, the solvents are evaporated off to yield the expected product in the form of crystals.

Elementary microanalysis:

|  | % C | % H | % N |
|---|---|---|---|
| calculated | 48.39 | 5.41 | 7.52 |
| found | 48.26 | 5.46 | 7.55 |

EXAMPLE 38

(±)-N-Acetyl-6-methyl-2-(3-pyridyl)-2,3-dihydro-4(1H)-pyridinone

The expected product is obtained according to the procedure described in Example 2, starting from the compound described in Example 36 and replacing the iodomethane by acetyl chloride.

EXAMPLE 39

(2R*,4S*,6R*)-N-Acetyl-6-methyl-2-(3-pyridyl)-4-piperidinol

The expected product is obtained according to the procedure described in Step A of Example 3, starting from the compound described in Example 38.

EXAMPLE 40

(2R*,4R*,6R*)-N-Acetyl-4-chloro-6-methyl-2-(3-pyridyl)-piperidine

Step A: (2R*,4S*,6R*)-N-Acetyl-6-methyl-2-(3-pyridyl)-4-piperidine

The expected product is obtained according to the procedure described in Step A of Example 12, starting from the compound described in Example 39.

Step B: (2R*,4R*,6R*)-N-Acetyl-4-chloro-6-methyl-2-(3-pyridyl)-piperidine

The expected product is obtained according to the procedure described in Step A of Example 13, starting from the compound obtained in the preceding Step.

EXAMPLE 41

(2R*,4S*,6R*)-N-Acetyl-6-methyl-4-methylthio-2-(3-pyridyl)-piperidine

The expected product is obtained according to the procedure described in Step A of Example 14, starting from the compound described in Example 40 and methanethiol.

EXAMPLE 42

(2R*,4S*,6R*)-N-Acetyl-4-methoxycarbonyloxy-6-methyl-2-(3-pyridyl)-piperidine

The expected product is obtained according to the procedure described in Example 4, starting from the compound described in Example 39 and replacing the iodomethane by methyl chloroformate.

EXAMPLE 43

(±)-N-Benzyl-6-propyl-2-(3-pyridyl)-2,3-dihydro-4(1H)-pyridinone

Step A: (±)-6-Propyl-2-(3-pyridyl)-2,3-dihydro-4(1H)-pyridinone

The expected product is obtained according to the procedure described in Example 1, starting from nicotinaldehyde and nonane-4,6-dione.

Step B. (±)-N-Benzyl-6-propyl-2-(3-pyridyl)-2,3-dihydro-4(1H)-pyridinone

The expected product is obtained according to the procedure described in Example 2, starting from the compound obtained in the preceding Step and replacing the iodomethane by benzyl chloride.

EXAMPLE 44

(±)-N-Benzyl-6-propyl-2-(3-pyridyl)-2,3-dihydro-4(1H)-pyridinone O-[2-(dimethylamino)-ethyl]-oxime The expected product is obtained according to the procedure described in Example 15, starting from the compound described in Example 43 and replacing the hydroxylamine hydrochloride by 2-(aminooxy)-N,N-dimethylethanamine.

Pharmacological Study of the Compounds of the Invention

EXAMPLE 45

Locomotion in the Wistar Rat

The effects of the compounds of the invention on motor activity were assessed in the adult male Wistar rat. Wistar rats (180–200 g) were treated (intraperitoneal route) with the compounds being studied or their carriers (2 ml/kg). Thirty minutes after pharmacological treatment, the animals were placed in an open-field (40×40×60 cm) located in a controlled-environment experimentation room. The motor activity of the animals was assessed by measuring the distance they covered (cm) in the open-field over 30 minutes. The measurement was carried out automatically by a video-surveillance system coupled to a micro-computer (Videotrack system, View-Point, France). The results were expressed as means plus or minus the standard errors of the means, and inter-group comparisons were made by a single-factor variance analysis test followed, where appropriate, by a Dunnett test.

The results show that the compounds of the invention do not have any activity on the locomotion in the rat at a dose of 10 mg/kg or below.

EXAMPLE 46
Body Temperature in the NMRI Mouse

The effects of the compounds of the invention on body temperature were assessed in the adult male NMRI mouse. The rectal temperature of the mice (18–20 g) was measured just before pharmacological treatment (intraperitoneal route) with the compounds being studied or their carriers (20 mg/kg). The mice were then placed in individual cages (10×10×10 cm) and their rectal temperature was measured every 30 minutes during the 2 hours following treatment. The values were the means (°C.) plus or minus the standard errors of the means, and inter-group comparisons were carried out by a single-factor variance analysis test followed, where appropriate by a Dunnett test.

The results show that the compounds of the invention do not have hypothermic activity at a dose of 20 mg/kg or below.

EXAMPLE 47
Abdominal Contractions Induced by Phenyl-p-Benzoquinone (PBQ) in the NMRI Mouse Intraperitoneal administration of an alcoholic solution of PBQ causes abdominal cramps in the mouse (SIEGNUND et al., Proc. Soc. Exp. Biol., 1957, 95, 729–731). The cramps are characterized by repeated contractions of the abdominal musculature, accompanied by extension of the hind limbs. Most analgesics antagonise these abdominal cramps (COLLIER et al., Brit. J. Pharmacol. Chem., 1968, 32, 295–310). At t=0 min., the animals are weight and the compound being studied is administered by the IP route. A group of contol animals is given the solvent used for the compound. At t=30 min., an alcoholic solution of PBQ (0.2%) is administered by the IP route in a volume of 0.25 ml/mouse. Immediately after administration of the PBQ, the animals are placed in cylinders of plexiglass (L=19.5 cm; I.D.=5 cm). From t=35 min. to t=45 min., the animals' reaction is observed and the experimenter notes the total number of abdominal cramps per animal. The Table hereinbelow gives the percentage inhibition of the number of abdominal cramps measured in the control animals, at the active dose of the compound studied. The results obtained show that the compounds of the invention possess antalgic properties.

| Example | Dose (mg/kg) | Inhibition (%) |
|---|---|---|
| 1 | 10 | 51 |
| 25 | 20 | 69 |
| 26 | 10 | 55 |
| 30 | 20 | 51 |

EXAMPLE 48
Social Recognition in the Wistar Rat

Initially described in 1982 by THOR and HOLLOWAY, (J. Comp. Physiol., 1982, 96, 1000–1006), the social recognition test has subsequently been proposed by various authors (DANTZER et al., Psychopharmacology, 1987, 91, 363–368; PERIO et al., Psycho-pharmacology, 1989, 97, 262–268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test by intraperitoneal route and, after 2 hours, is again brought into the presence (5 minutes) of the young rat. The social recognition behaviour is then observed again and its duration measured.

The Table hereinbelow gives the difference ($T_2 - T_1$), expressed in seconds, between the "recognition" times of the 2 encounters. The results obtained show that the compounds of the invention very greatly enhance memorisation, even at a low dose.

| Example | Dose (mg/kg) | $T_2 - T_1$ (s) |
|---|---|---|
| 1 | 3 | −36 |
| 21 | 3 | −33 |
| 24 | 3 | −32 |
| 36 | 3 | −36 |

EXAMPLE 49
Object Recognition in the Wistar Rat

The object recognition test in the Wistar rat was initially developed by ENNACEUR and DELACOUR (Behav. Brain Res., 1988, 31, 47–59). The test is based on the spontaneous exploratory activity of the animal and has he characteristics of episodic memory in humans. This memory test is sensitive to ageing (SCALI et al., Eur. J. Pharmacol., 1997, 325, 173–180) and to cholinergic dysfunctions (BARTOLINI et al., Pharm. Biochem. Behav. 1996, 53(2), 277–283) and is based on the differences in the exploration of 2 objects of fairly similar shape—one familiar, the other new. Prior to the test, the animals are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the IP route or p.o. 30 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered.

The Table hereinbelow gives the difference, Delta, expressed in seconds, between the exploration times of the 2 objects. The results obtained show that the compounds of the invention greatly enhance memorisation, even at a very low dose, not only by i.p. but also by p.o. route.

| Example | Dose (mg/kg) | Delta (s) | Route |
|---|---|---|---|
| 1 | 0.3 | 7.5 | i.p. |
|  | 0.3 | 9.95 | p.o. |
| 18 | 1 | 6.2 | p.o. |
| 22 | 0.3 | 9.98 | i.p. |
|  | 3 | 5.93 | p.o. |
| 24 | 3 | 7.55 | i.p. |
| 27 | 3 | 6.68 | i.p. |

EXAMPLE 50

Pharmaceutical Composition

Formulation for the preparation of 1000 tablets each comprising 10 mg of active ingredient:

| | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I):

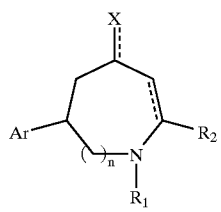

(I)

wherein:

n represents 1, $R_1$ represents hydrogen, aryl-$(C_1-C_6)$alkyl in which the alkyl moiety is linear or branched, linear or branched $(C_1-C_6)$alkyl, linear or branched $(C_1-C_6)$acyl, linear or branched $(C_1-C_6)$alkoxycarbonyl, aryl-$(C_1-C_6)$ alkoxycarbonyl in which the alkoxy moiety is linear or branched, or trifluoroacetyl, $R_2$ represents linear or branched $(C_1-C_6)$alkyl, X represents oxygen, chlorine, $OR_3$, $SR_4$ or $NOR_5$, wherein $R_3$ represents hydrogen, linear or branched $(C_1-C_6)$ alkyl, linear or branched $(C_1-C_6)$acyl, linear or branched $(C_1-C_6)$alkoxycarbonyl, or aryl-$(C_1-C_6)$ alkoxycarbonyl in which the alkoxy moiety is linear or branched, $R_4$ represents hydrogen, linear or branched $(C_1-C_6)$ alkyl, or aryl, $R_5$ represents hydrogen or linear or branched $C_1-C_6$) alkyl optionally substituted by one or more identical or different groups selected from hydroxy, amino (optionally substituted by one or two linear or branched $C_1-C_6$)alkyl groups), and linear or branched $C_1-C_6$)alkoxy, === represents a single or double bond, it being understood that the valency of the atoms is respected, Ar represents aryl or heteroaryl, its isomers and addition salts thereof with a pharmaceutically-acceptable acid, on the understanding that the term "aryl" means phenyl, biphenylyl, naphthyl, or tetrahydronaphthyl, each of those groups being optionally substituted by one or more identical or different groups selected from halogen, linear or branched $C_1-C_6$)alkyl, hydroxy, linear or branched $C_1-C_6$)alkoxy, trihalomethyl, and amino (optionally substituted by one or more linear or branched $C_1-C_6$)alkyl groups), and that the term "heteroaryl" denotes an aromatic, mono- or bi-cyclic, 5- to 12-membered group containing one, two or three hetero atoms selected from oxygen, nitrogen and sulphur, it being understood that the heteroaryl group may be optionally substituted by one or more identical or different groups selected from halogen, linear or branched $C_1-C_6$) alkyl, hydroxy, linear or branched $C_1-C_6$)alkoxy, trihalomethyl, and amino (optionally substituted by one or more linear or branched $C_1-C_6$)alkyl groups).

2. A compound of claim 1 wherein X represents oxygen or $OR_3$ wherein $R_3$ is as defined in claim 1.

3. A compound of claim 1, wherein X represents $NOR_5$ wherein $R_5$ is as defined in claim 1.

4. A compound of claim 1, wherein X represents $SR_4$ wherein $R_4$ is as defined in claim 1.

5. A compound of claim 1, wherein X represents chlorine.

6. A compound of claim 2, wherein X represents oxygen or $OR_3$ wherein $R_3$ represents hydrogen.

7. A compound of claim 1 wherein $R_1$ represents hydrogen.

8. A compound of claim 1, wherein Ar represents optionally substituted phenyl.

9. A compound of claim 1, wherein Ar represents optionally substituted thienyl.

10. A compound of claim 1, wherein Ar represents optionally substituted pyridyl.

11. A compound of claim 1 which is (±)-6-(4-chlorophenyl)-2-methyl-1,5,6,7-tetrahydro-4H-azepin-4-one.

12. A Method for treating a mammal afflicted with a condition requiring an antalgic agent or a facilitator of memory and cognition, comprising the step of administering to the mammal an amount of a compound of claim 1 which is effective for alleviation of said condition.

13. A pharmaceutical composition comprising as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO.    : 6,451,789 B1
DATED         : September 17, 2002
INVENTOR(S)   : Sylvain Rault et al.

It is certified that error appears in the above-identified patent and that said Letters Patent is hereby corrected as shown below:

Title page,
Item [54], "1-AZA-2-ALKY-6-ARYL-CYCLOALKANES" should be
-- 1-AZA-2-ALKYL-6-ARYL-CYCLOALKANES --.

Column 22,
Lines 1, 5, 6, 15, 16, 18, 24, 25 and 27, "$C_1$-$C_6$)" should be -- ($C_1$-$C_6$) --.

Signed and Sealed this

Fourth Day of March, 2003

JAMES E. ROGAN
*Director of the United States Patent and Trademark Office*